(12) United States Patent
Vijfvinkel

(10) Patent No.: US 10,470,651 B2
(45) Date of Patent: Nov. 12, 2019

(54) EYE SURGICAL LIGHTING UNIT

(71) Applicant: D.O.R.C. Dutch Ophthalmic Research Center (International) B.V., Zuidland (NL)

(72) Inventor: Gerrit Jan Vijfvinkel, Zuidland (NL)

(73) Assignee: D.O.R.C. DUTCH OPHTHALMIC RESEARCH CENTER (INTERNATIONAL) B.V., Zuidland (NL)

( * ) Notice: Subject to any disclaimer, the term of this patent is extended or adjusted under 35 U.S.C. 154(b) by 456 days.

(21) Appl. No.: 14/383,694

(22) PCT Filed: Mar. 11, 2013

(86) PCT No.: PCT/NL2013/050156
§ 371 (c)(1),
(2) Date: Sep. 8, 2014

(87) PCT Pub. No.: WO2013/133717
PCT Pub. Date: Sep. 12, 2013

(65) Prior Publication Data
US 2015/0018629 A1  Jan. 15, 2015

(30) Foreign Application Priority Data
Mar. 9, 2012  (NL) .................................. 2008455

(51) Int. Cl.
*A61B 3/00* (2006.01)
*A61B 90/35* (2016.01)
(Continued)

(52) U.S. Cl.
CPC .......... *A61B 3/0008* (2013.01); *A61B 5/0084* (2013.01); *A61B 90/30* (2016.02);
(Continued)

(58) Field of Classification Search
CPC ........ A61B 90/30; A61B 90/35; A61B 3/0008
(Continued)

(56) References Cited

U.S. PATENT DOCUMENTS

| 4,102,342 A | 7/1978 | Akiyama |
| 5,275,593 A | 1/1994 | Easley |
(Continued)

FOREIGN PATENT DOCUMENTS

| EP | 1844705 A1 | 10/2007 |
| JP | 2002-540887 A | 12/2002 |
(Continued)

OTHER PUBLICATIONS

International Search Report from PCT/NL2013/050156 dated Jul. 1, 2013.

*Primary Examiner* — Zade Coley
*Assistant Examiner* — Amy R Sipp
(74) *Attorney, Agent, or Firm* — Adsero IP

(57) ABSTRACT

The invention relates to an eye surgical lighting unit for lighting internal ocular tissue. The lighting unit comprises a fiber having a proximal end and a distal end, for guiding a light beam to the distal end. The lighting unit also comprises a manual unit, provided with a cannula and a handle having an internal passage positioned in line with the cannula. The fiber is adjustable between an intraocular operational position in which the fiber extends through the internal passage of the handle and through the cannula, and a chandelier operational position in which the fiber is uncoupled from the manual unit.

2 Claims, 3 Drawing Sheets

(51) Int. Cl.
*A61B 5/00* (2006.01)
*A61B 90/30* (2016.01)
*A61F 9/007* (2006.01)

(52) U.S. Cl.
CPC ........ *A61B 90/35* (2016.02); *A61B 2090/306* (2016.02); *A61F 9/00736* (2013.01)

(58) Field of Classification Search
USPC ................................. 600/249; 362/389, 655
See application file for complete search history.

(56) References Cited

U.S. PATENT DOCUMENTS

| | | | |
|---|---|---|---|
| 5,478,338 A | 12/1995 | Reynard | |
| 5,588,952 A | 12/1996 | Dandolu | |
| 5,643,253 A | 7/1997 | Baxter | |
| 5,681,264 A * | 10/1997 | Ryan, Jr. | A61B 3/0008 362/344 |
| 5,725,514 A | 3/1998 | Grinblat | |
| 5,916,149 A * | 6/1999 | Ryan, Jr. | A61B 5/0059 362/344 |
| 6,015,403 A | 1/2000 | Jones | |
| 6,036,678 A | 3/2000 | Giungo | |
| 6,106,162 A | 8/2000 | Markovich | |
| 6,428,553 B1 * | 8/2002 | Trese | A61F 9/00736 606/16 |
| 6,494,878 B1 | 12/2002 | Pawlowski | |
| 7,229,202 B2 | 6/2007 | Sander | |
| 7,704,246 B2 | 4/2010 | Connor | |
| 7,783,346 B2 | 8/2010 | Smith | |
| 2003/0169603 A1 | 9/2003 | Luloh | |
| 2005/0245916 A1 | 11/2005 | Connor | |
| 2007/0255264 A1 | 11/2007 | Hickingbotham | |
| 2008/0287938 A1 * | 11/2008 | Scheller | A61B 18/22 606/15 |
| 2011/0245787 A1 | 10/2011 | Zica | |

FOREIGN PATENT DOCUMENTS

| | | |
|---|---|---|
| WO | WO 1998/022805 | 5/1998 |
| WO | WO 2000/61023 | 10/2000 |

* cited by examiner

EYE SURGICAL LIGHTING UNIT

RELATED APPLICATIONS

This application is a 35 U.S.C. § 371 national phase application of PCT/NL2013/050156 (WO 2013/133717), filed on Mar. 11, 2013, entitled "Eye Surgical Lighting Unit", which application claims priority to Netherlands Application No. 2008455, filed Mar. 9, 2012, which is incorporated herein by reference in its entirety.

The invention relates to an eye surgical lighting unit for lighting internal ocular tissue, comprising a fiber having a proximal end and a distal end, for guiding a light beam to the distal end, wherein the lighting unit furthermore comprises a manual unit, provided with a cannula and a handle having an internal passage positioned in line with the cannula.

Such an eye surgical lighting unit is known for performing ophthalmic operations. A light source is connected to the proximal end of the fiber, so that the light generated by the light source can propagate through the fiber and exits from the fiber via the distal end thereof. During an eye surgical procedure the distal end of the fiber can be brought into the eye, so that the ocular tissue to be treated is effectively lighted.

In a lighting unit from the prior art, the fiber extends through the internal passage of the handle and the cannula aligned therewith. The distal end of the fiber is brought into the interior of the eye via the cannula of a trocar. By manually adjusting the position and/or orientation of the cannula in the eye, the surgeon can realize a lighting desired at that moment. The lighting that such a lighting unit generates is also referred to as intraocular lighting.

Also, from the European patent publication EP 1 844 705 a lighting unit is known without integrated manual unit. The fiber is provided with a stop displaceable along the outer covering of the fiber in order for the fiber to extend into the eye by a preset penetration depth, via a cannula of a trocar, arranged in the ocular wall. The lighting that such a lighting unit generates is also referred to as chandelier lighting to facilitate so-called bimanual surgery.

It is noted that United States patent publication US 2011/245787 describes a trocar cannula.

The invention contemplates providing an eye surgical lighting unit of the kind mentioned in the opening paragraph hereof, whereby the functionality is augmented. To this end, the fiber of the lighting unit according to the invention is adjustable between an intraocular operational position in which the fiber extends through the internal passage of the handle and through the cannula, and a chandelier operational position in which the fiber is uncoupled from the manual unit.

By designing the fiber to be adjustable with respect to the manual unit, the lighting unit can serve both as intraocular lighting and as 10 chandelier lighting. If intraocular lighting is desired, the fiber can be threaded through the handle and the cannula, and the distal end of the fiber can be brought via the cannula of a trocar into the eye so that a desired position and/or orientation of the distal fiber end can be accurately taken up through operation of the handle. If, on the other hand, a chandelier lighting 15 is desired, the fiber can be uncoupled from the manual unit, so that the distal end of the fiber can be introduced via a cannula of a trocar, arranged in the ocular wall. Thus, the lighting unit has a dual function, viz., as intraocular lighting and as chandelier lighting.

Preferably, the proximal end is provided with a connector for connection to a light source, so that the fiber is connectable to different types of light sources. Alternatively, the proximal end of the fiber may be provided with an integrated light source.

By furthermore providing a stop which is movable along the outer surface of the fiber, the penetration depth of the fiber—in the use as chandelier lighting—can be set beforehand by the surgeon, to obtain a desired light distribution in the eye. Alternatively, the stop is fixed at a specific position along the fiber, or the fiber is designed without stop.

The lighting unit can have a fixation element to fix the fiber in the intraocular operational position in a direction along the cannula. This prevents the fiber shifting back and forth in the manual unit, or even sliding out of the manual unit at an undesired moment.

The invention will be further elucidated on the basis of an exemplary embodiment which is represented in the drawings. In the drawings.

The drawings show only a schematic representation of a preferred mode of the invention. In the Figures, like or corresponding parts are denoted with the same reference numerals.

Figure 1:
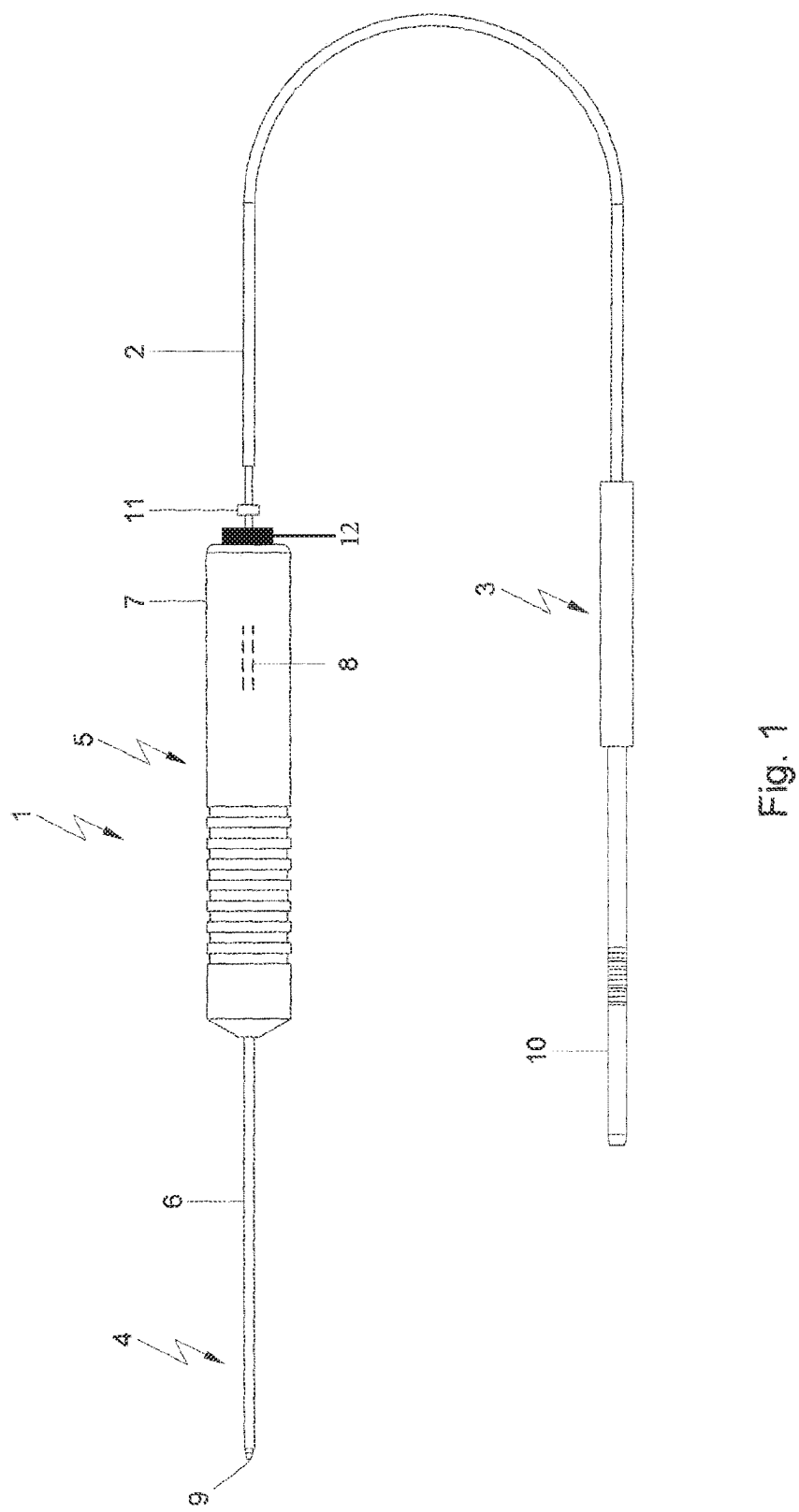
FIG. 1 shows a schematic elevational view of a lighting unit according to the invention in an intraocular operational position.

FIG. 1 shows an eye surgical lighting unit 1 according to the invention, for lighting internal ocular tissue. The lighting unit 1 has a fiber 2 with a proximal end 3 and a distal end 4, for guiding a light beam to the distal end 4. The lighting unit 1 also has a manual unit 5 with a cannula 6 and a handle 7 having an internal passage 8 positioned in line with the cannula 6. The fiber 2 is adjustable between different operational positions.

In FIG. 1 the fiber 2 is in an intraocular operational position. The fiber 2 extends through the internal passage 8 of the handle 7 and through the cannula 6. The tip 9 of the distal fiber end 4 extends slightly beyond the cannula 6, so that the light beam exiting there can light internal ocular tissue when the cannula penetrates via a trocar through the ocular wall.

The lighting unit 1 as shown in FIG. 1 is in principle ready for use as intraocular lighting.

The handle is shaped and dimensioned such that the user through operation thereof can bring the distal end 4 of the fiber 2 accurately in a desired position and/or orientation, so that a specifically desired lighting in the eye can be realized. To this end, the handle is designed such that through manual operation thereof the distal end of the fiber can be threaded through a trocar.

The proximal end 3 of the fiber is provided with a connector 10 for connection to a light source (not shown). Furthermore, the lighting unit has a stop 11 which is displaceable along the outer surface of the fiber 2, near the distal end 4. Also, the lighting unit has a fixation element 12, such as a fixation screw, to fix the fiber in the intraocular operational position in a direction R along the cannula 6.

The fiber 1 has an outer diameter size of 25 G, the cannula 6 has an outer diameter size of 23 G. Obviously, other dimensionings are also possible, for example, greater than or less than the diameter sizes mentioned.

Figure 2:
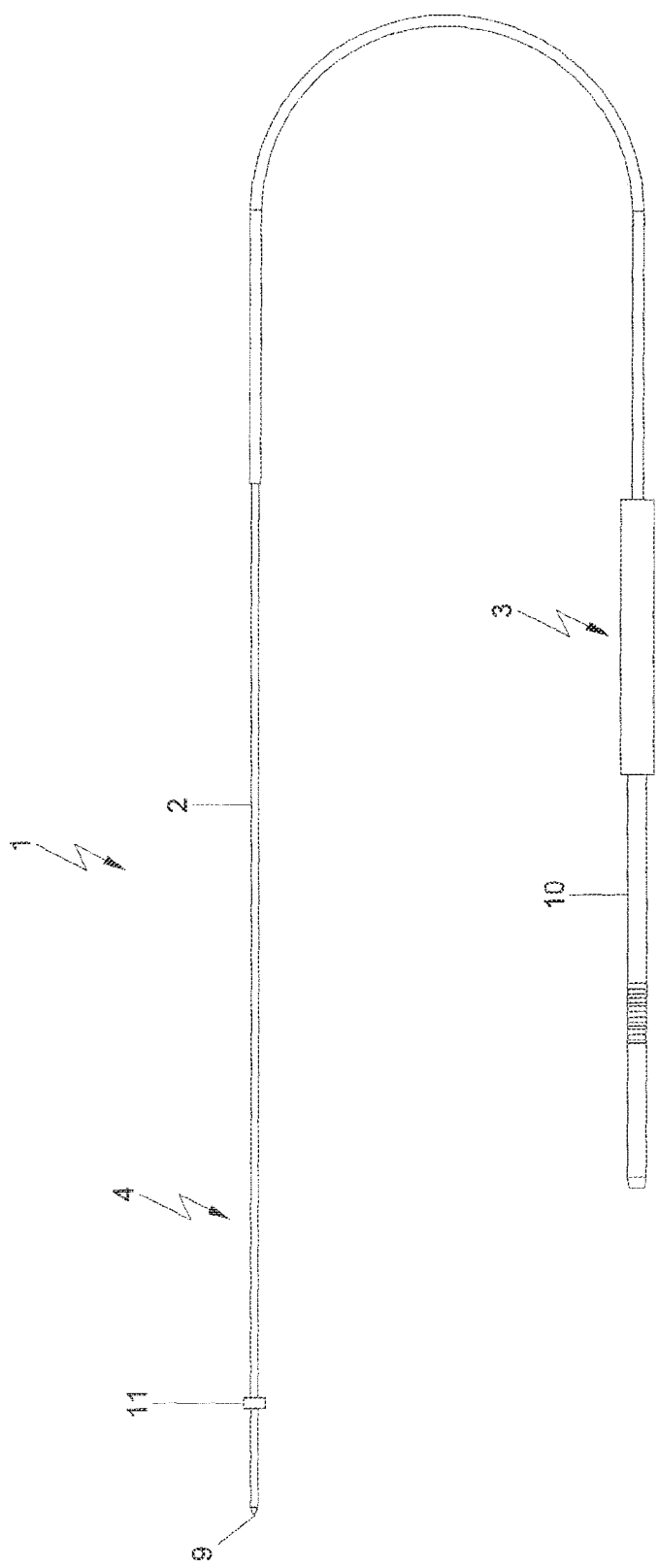
FIG. 2 shows a schematic elevational view of the lighting unit from FIG. 1 in a chandelier operational position.

FIG. 2 shows a schematic elevational view of the lighting unit 1 in a chandelier operational position. The fiber 2 is here uncoupled from the manual unit 5. The distal end 4 of the fiber 2 can be positioned internally in the eye via a trocar cannula, also called entry, arranged in the ocular wall. Thus a chandelier lighting can be realized, in support of bimanual surgery.

Figure 3:
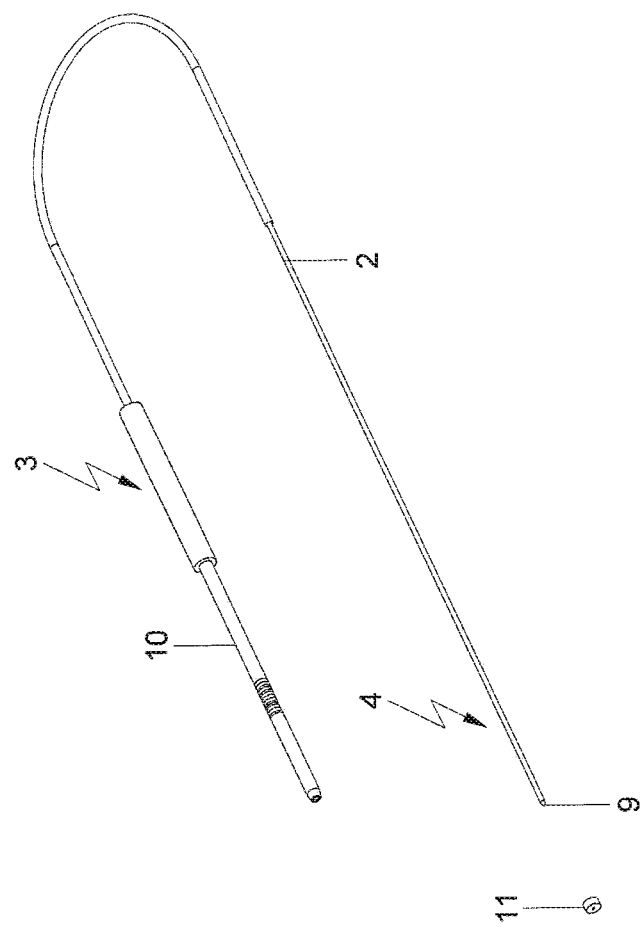
FIG. 3 shows a schematic elevational view of the lighting unit from FIG. 1 in disassembled condition.
Figure 3:
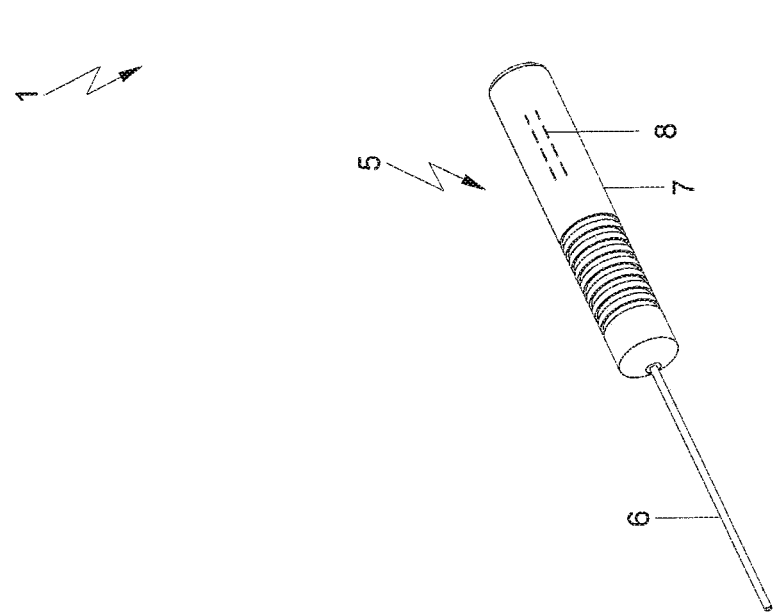

FIG. 3 shows a schematic elevational view of the lighting unit 1 in disassembled condition.

The lighting unit can be brought from the chandelier operational position to the intraocular operational position by threading the distal end 4 of the fiber 2 through the internal passage 8 of the handle 7 and through the cannula 6 of the manual unit 5. When the fiber 2 is provided with a stop 11, the stop, prior to threading in, can be moved over some distance towards the proximal end 3 of the fiber to facilitate threading in.

The lighting unit can be brought from the intraocular operational position to the chandelier operational position by withdrawing the distal end 4 of the fiber 2 from the cannula 6 and the handle 7 of the manual unit 5.

In both the intraocular operational position and the chandelier operational position, the distal end 4 of the fiber 2 of the lighting unit 1 is preferably brought into the interior of the eye via a trocar.

The invention is not limited to the exemplary embodiments described here. Many variants are possible. Thus, the outer surface of the fiber 2 may be provided with a protective top layer.

Such variants will be clear to one of ordinary skill in the art and are understood to be within the scope of the invention, as set forth in the following claims.

The invention claimed is:

1. A method for adjusting an eye surgical lighting unit, the method comprising: providing an eye surgical lighting unit having a fiber having a proximal end and a distal end for guiding a light beam to the distal end, the lighting unit furthermore having a manual unit provided with a cannula and a handle having an internal passage positioned in line with the cannula, wherein the fiber is adjustable between an intraocular operational position in which the fiber extends through the internal passage of the handle and through the cannula, and a chandelier operational position in which the fiber is disassembled from the manual unit; and adjusting from the chandelier operational position to the intraocular operational position by threading the distal end of the fiber through the internal passage of the handle and through the cannula of the manual unit, wherein, when the fiber is in the chandelier operational position, the lighting unit provides chandelier lighting for bimanual ophthalmic surgery, and wherein, when the fiber is in the intraocular position, the lighting unit provides intraocular lighting for ophthalmic surgery.

2. A method for adjusting an eye surgical lighting unit, the method comprising: providing an eye surgical lighting unit having a fiber having a proximal end and a distal end for guiding a light beam to the distal end, the lighting unit furthermore having a manual unit provided with a cannula and a handle having an internal passage positioned in line with the cannula, wherein the fiber is adjustable between an intraocular operational position in which the fiber extends through the internal passage of the handle and through the cannula, and a chandelier operational position in which the fiber is disassembled from the manual unit; and adjusting from the intraocular operational position to the chandelier operational position by withdrawing the distal end of the fiber from the cannula and the handle of the manual unit, wherein, when the fiber is in the intraocular position, the lighting unit provides intraocular lighting for ophthalmic surgery, and wherein, when the fiber is in the chandelier operational position, the lighting unit provides chandelier lighting for bimanual ophthalmic surgery.

\* \* \* \* \*